US009683243B2

(12) United States Patent
Hennart (10) Patent No.: US 9,683,243 B2
(45) Date of Patent: Jun. 20, 2017

(54) CAPSICUM ROOTSTOCK (75) Inventor: Jean Winoc Hennart, Nimes (FR)

(73) Assignee: VILMORIN, La Menitre (FR)

( * ) Notice: Subject to any disclaimer, the term of this patent is extended or adjusted under 35 U.S.C. 154(b) by 462 days.

(21) Appl. No.: 14/008,991

(22) PCT Filed: Mar. 29, 2012

(86) PCT No.: PCT/FR2012/050664
§ 371 (c)(1),
(2), (4) Date: Dec. 16, 2013

(87) PCT Pub. No.: WO2012/131262
PCT Pub. Date: Oct. 4, 2012

(65) Prior Publication Data
US 2014/0096289 A1    Apr. 3, 2014

(30) Foreign Application Priority Data
Mar. 31, 2011 (FR) .................... 11 52772

(51) Int. Cl.
*A01H 1/02* (2006.01)
*A01H 5/08* (2006.01)
*A01G 1/06* (2006.01)
*C12N 15/82* (2006.01)
*A01H 5/00* (2006.01)

(52) U.S. Cl.
CPC ........... *C12N 15/8285* (2013.01); *A01H 1/02* (2013.01); *A01H 5/00* (2013.01); *A01H 5/08* (2013.01); *C12N 15/8282* (2013.01); *A01G 1/06* (2013.01)

(58) Field of Classification Search
None
See application file for complete search history.

(56) References Cited

PUBLICATIONS

Yoon et al. Breeding Science 56: 31-38 (2006).*
Rodriguez-Burruezo et al. Euphytica 170(1-2): 169-181 (Nov. 2009).*
Foster et al. Plant Disease 94(1): 24-30 (Jan. 2010).*
Carlos Eduardo da Silva Monteiro et al. (2011). Reproductive characterization of interspecific hybrids among *Capsicum* species. *Crop Breeding and Applied Biotechnology*, 11, 241-249.
William A. Emboden Jr. (1964). A Preliminary Study of the Crossing Relationships of *Capsicum baccatum*. *Butler University Botanical Studies*, 14(2), 1-5.
Mirjana Mijatovic et al. (2005). Diseases of pepper in Serbia and results of breeding for resistance. *Folia Horticulturae, Ann.* 17(2), 53-60.
Cristina Duda de Oliveira et al. (2009). Resistência de pimentos a nematóides de galha e compatibilidade enxerto/porta-enxerto entre hibridos de pimentão e pimentos. *Horticulture Bresileira*, 27(4), 620-526.

International Search Report, mailed Jul. 2, 2012 in connection with PCT International Application No. PCT/FR2012/050664, filed Mar. 29, 2012 [including English language translation].
Erard, P., & Odet, J. (2008). Le poivron—Intérêt limite du greffage. *Infos-Ctifl*, 238, 31-35.
Palada, M. C., & Wu, D. L. (2008). Evaluation of Chili Rootstocks for Grafted Sweet Pepper Production during the Hot-wet and Hot-dry Seasons in Taiwan. *Acta Hort.* (*ISHS*), 767, 151-157.
Ribeiro, C. S. d. C. et al. (2003). Evaluation of *Capsicum* spp. Genotypes for resistance to *Phytophthora capsici* in Brazil. *Capsicum and Eggplant Newsletter*, 22, 125-126.
Yoon, J. B. et al. (2009). Inheritance of Anthracnose (*Colletotrichum acutatum*) Resistance in *Capsicum* using Interspecific Hybridization. *Kor. J. Hort. Sci. Technol.*, 27(1), 140-144.
Egawa, Y., & Tanaka, M. (1986). Cytogenetical Study of the Interspecific Hybrid between *Capsicum annuum* and *C. baccatum*. *Japan. J. Breed.*, 36, 16-21.
Jones, M. M., & Black, L. L. (1992). Sources of Resistance among *Capsicum* spp. to Fusarium Wilt of Pepper. *Capsicum Newsletter*, 11, 33-34.
Ortega, G. et al. (1990). Search for Verticillium dahliae resistance in *Capsicum* sp. *Capsicum Newsletter*, 8-9, 60-61.
Muhyi, R., & Bosland, P. W. (1995). Evaluation of *Capsicum* Germplasm for Sources of Resistance to *Rhizoctonia solani*. *HortScience*, 30(2), 341-342.
Dumas de Vaulx, R. (1992). Culture d'embryons et d'ovaires fécondés. In J. Jahier (Ed.), *Techniques de cytogénétique végétate* (p. 141). INRA Editions.
Djian-Caporalino, C. et al. (2007). Root-knot nematode (*Meloidogyne* spp.) Me resistance genes in pepper (*Capsicum annuum* L.) are clustered on the P9 chromosome. *Theor. Appl. Genet.*, 114, 473-486.
Wang, L. H. et al. (2009). A SCAR marker linked to the N gene for resistance to root knot nematodes (*Meloidogyne* spp.) in pepper (*Capsicum annuum* L.). *Scientia Horticulture*, 122, 318-322.
Eshbaugh W. Hardy, 1970, A Biosystematic and Evolutionary Study of Capsicum Baccatum (Solanaceae), Brittonia, 22, pp. 31-43.
Cheng et al. (2007) "Interspecific Hybridization and Indentification of Hybrid in Capsicum," Acta Horticulturae Sinica, 34(4), pp. 883-888 (including English translation).
Janos Taller et al. (1999) "Graft-induced variants as a source of novel charactersitics in the breeding of pepper (*Capsicum annum* L.)" Euphytica, vol. 18, pp. 73-78.
Jae Bok Yoon et al. (2004) "Interspecific Cross Compatibility among Five Domesticated Species of *Capsicum* Genus", Journal of The Korean Society For Horticultural Science vol. 45, No. 6, pp. 324-329.

(Continued)

*Primary Examiner* — David T Fox
(74) *Attorney, Agent, or Firm* — John P. White; Cooper & Dunham LLP (57) ABSTRACT The present invention relates to a plant from the *Capsicum* family suitable for use as rootstock, capable of being obtained from the initial crossing of a *Capsicum* plant, preferably a *C. annuum* plant, with a *Capsicum baccatum* plant used as female parent, optionally followed by one or more additional crossing(s) with a *Capsicum baccatum* plant. Another subject of the present invention is a grafted plant constituted of a rootstock according to the invention and a graft. A further subject of the present invention is a seed, a cell or a part of a rootstock plant according to the invention. A final subject of the present invention is the use of a plant according to the invention as rootstock and a process for obtaining a grafted plant.

17 Claims, 5 Drawing Sheets (56) References Cited

PUBLICATIONS

Oka Y et al. (2004) "Pepper Rootstock Graft Compability and Response to Meloidogyne Javanica and M. Incognita" Journal of Nematology, vol. 36, No. 2, pp. 137-141.

Bapa Rao N. et al. (1992) "Cytogenetic studies on the interspecific hybrid Capsicum baccatum L. × C. frutescens L. and its progeny" Euphytica, vol. 59, pp. 135-140.

Egawa Y., Tanaka M. (1984) "Cytogenetical Relationships among Three Species of Chili Peppers, Capsicum chinense, C.frutescens and C.baccatum" Japan J. Breed., vol. 34, pp. 50-56.

Casali V. W. D., Couto F. A. A. (1984) "Origin and botany of Capsicum." Informe Agropecuario, vol. 10, No. 113, pp. 8-10.

Tong N., Bosland P. W. (1999) "Capsicum tovarii, a new member of the Capsicum baccatum complex" Euphytica, vol. 109, pp. 71-77.

Dumas de Vaulx, R. et al. (1977) "Interspecific crossing between C. annuum and C. Baccatum" Capsicum 77: report of the third Eucarpia congress on the genetics and breeding of red pepper, Jul. 1977, Avignon-Montfavet, France, pp. 5-8.

\* cited by examiner

CAPSICUM ROOTSTOCK

CROSS-REFERENCE TO RELATED APPLICATIONS

This application is a §371 national stage of PCT International Application No. PCT/FR2012/050664, filed Mar. 29, 2012, claiming priority of French Patent Application No. 1152772, filed Mar. 31, 2011, the contents of each of which are hereby incorporated by reference in their entirety.

This invention relates to a plant of the *Capsicum* family (chili peppers, sweet peppers) suitable for use as a rootstock.

Chili peppers and sweet peppers belong to the large Solanaceae family (also including in particular tomatoes, potatoes and aubergines) of tropical origin, and encompass both sweet peppers (or "sweet peppers") and peppers with a more or less burning flavour and containing capsaicin.

The cultivated pepper, *Capsicum annuum*, belongs to the *Capsicum* genus. Other *Capsicums*, more or less compatible with *Capsicum annuum*, but also with one another, exist, in particular *Capsicum pubescens, Capsicum baccatum, Capsicum chinense* and *Capsicum frutescens*.

Since the 1970's, global pepper production has continuously increased, in particular in China and Turkey. Europe maintains a good level of production, especially Spain, but also the Netherlands and Italy.

There are a wide variety of modes of pepper production. In the summer in temperate climates or in the dry season in tropical climates, peppers are cultivated in the open field. The yields vary from 10 t/ha to more than 100 t/ha depending on whether the fruits are small or large.

Sheltered crop production makes it possible to extend the production period by beginning the crop period early, but also by producing in the off-season in Mediterranean countries (Spain, Italy, Turkey, Israel, etc.). Farther north, in the Netherlands, greenhouse crops make it possible to produce for more than 10 months of the year and to achieve very high yields.

In field-grown crop production, but also in sheltered crop production, since the removal of methyl bromide from the list of authorized soil sterilization products in 2005, pepper producers have been faced with problems concerning telluric pathogens, in particular soil fungi and nematodes.

Various means of protection are still available, for example, soil sterilization with steam or solarization, but they are not optimal and are difficult to use. Crop rotation is also a possibility, but it is unsuitable for intensive sheltered crop production. Soil-less culture may become an option, but it is technically sophisticated and requires additional investments and moreover does not rule out contamination.

Seed growers are working to develop varieties that are tolerant of or resistant to the main parasites, which are *Phytophthora capsici, Rhizoctonia solani* (often in association with *Fusarium solani*) and *Meloidogyne* spp. (*Meloidogyne incognita, Meloidogyne arenaria, Meloidogyne javanica* and *Meloidogyne hapla*). However, there are currently no varieties of pepper or sweet pepper that combine both resistance and agronomic qualities (in particular the vigour, the yield and the fruit quality) sufficiently for commercialization. Chili pepper and sweet pepper producers therefore need new options.

To date, *C. baccatum* is a species rarely used by breeders seeking to improve the *C. annuum* species, for two reasons. First, *C. baccatum* is not known to exhibit valuable phenotypic traits, aside from resistance to anthracnose, which can be transferred to plants of the *C. annuum* species. Some resistances, such as to *Verticillium* and *Fusarium* have been identified in *C. baccatum*. However, these diseases are not major pathogens of the pepper. Moreover, the difficulty of crossing *C. baccatum* with *C. annuum*, related to incompatibilities between the two species, negates the value of these approaches.

The grafting of the pepper onto resistant varieties, developed only several years ago, may be used to provide a certain level of resistance to telluric pathogens such as *Phytophthora*, or even to certain nematodes. Grafting is intended to prevent contact between the plant to be cultivated and the infested soil. The variety of interest used as the "graft", optionally an F1 hybrid, is grafted onto the resistant plant used as the "rootstock". The resistant rootstock remains healthy and provides, from the soil, a normal supply for the graft that it isolates from the disease-carrying telluric inoculum.

The qualities of the aerial apparatus of the graft are therefore combined with those of the root system of the rootstock.

Grafting must satisfy a twofold objective: in priority, to isolate the sensitive plant from the risk of contamination by telluric pathogens, and to maintain, and if possible improve, the agronomic value of the variety.

Concerning species of the *Capsicum* genus, the choice of plants capable of being used at present as a rootstock is limited to the *Capsicum* genus. Consequently, the current rootstocks are lines and hybrids of *Capsicum annuum* or even possibly interspecific hybrids of *Capsicum annuum* and *Capsicum chinense* (see Erard P. & Odet J., 2009 (1)). Thus, predominantly, the pepper rootstock solutions available use genetic resources belonging to the *C. annuum* species.

Palada & Wu, 2008 (2) tested the effect of the use, as rootstocks, of various varieties of *Capsicum* plants, including a *C. baccatum* plant, on flood tolerance in a tropical region. However, the yield values and the sizes of the fruit obtained with *C. baccatum* as a rootstock are lower than those of ungrafted plants.

One of the objectives of the breeders is to improve or maintain the balance between vegetative development, i.e. the development of the plant by growing roots, leaves and the stem, and generative development, i.e. the development of the plant by floral initiation and setting. Vegetative development in particular increases the vigour and resistance to stress of the plant, while significant generative development improves the yield and the quality of the fruit.

In the ungrafted pepper, the balance between vegetative and generative development of plants is very fragile and difficult to achieve in breeding and cultivation.

Cultivated chili pepper and sweet pepper plants generally have an imbalance toward the generative, associated in particular with the selection process, promoting in particular the increase in the size of the fruit. Thus, the majority of *C. annuum* plants currently cultivated commonly have a weak root system, more sensitive to telluric parasites or other types of stresses (saline stress, soil fatigue, etc.). These plants are thus highly generative and insufficiently vegetative.

In the grafted pepper, maintenance of the balance between generative and vegetative development requires even greater technical sophistication. With the rootstocks currently proposed, grafted pepper crops often have low vegetative and excessive generative development and require the suppression of fruit in order to revitalize the crop. The current rootstocks do not therefore provide any advantage with regard to the development of the plant, and in particular its root system or its productivity.

Thus, the current rootstocks, although they may provide solutions to certain intermediate soil parasite resistances (resistances present in the *C. annuum* species) do not improve the agronomic value of the grafted plant and in particular the equilibrium between vegetative and generative development.

Consequently, the advantages in terms of resistance of the current rootstocks are insufficient for obtaining a grafted plant having an acceptable commercial value. Those who carry out selection are therefore faced with the problem of obtaining a grafted plant in which the rootstock would be more vegetative while the graft would be more generative. Consequently, grafting has not been developed for the *Capsicum* species crop.

Obtaining highly-vegetative rootstocks would make it possible in particular to cultivate, in the open field, plants grafted with *C. annuum* grafts, which are not suitable as an open-field crop in ungrafted form due to an excessive imbalance toward generative development, this imbalance leading to increased sensitivity to various stresses.

The inventors have developed *Capsicum* plants combining resistance, vigour and/or a productivity gain capable of being used advantageously as rootstocks, which makes it possible to profit from the use of grafting in pepper cultivation.

The inventors have in effect successfully developed *Capsicum baccatum* plants suitable for use as rootstocks, in association in particular with *Capsicum annuum* grafts.

The inventors have in particular overcome two major obstacles faced by a person skilled in the art seeking to develop a pepper rootstock combining resistance to telluric pathogens, in particular *Phytophthora capsici* and *Meloidogyne* (nematodes), with improved vigour (production of the vegetative parts of the plant: roots, leaves and stems). It is very likely that their yield (fruit production) is likewise improved. These plants therefore have a better balance between vegetative aspects, in particular better root development, and generative aspects, in particular fruit production.

The first of these obstacles lies in the fact that *C. baccatum* plants are known not to be resistant to *Phytophthora capsici* or to *Meloidogyne*. In particular, a study by Embrapa (3) demonstrates the lack of resistance to *Phytophthora capsici* in the species. Thus, a person skilled in the art seeking to create rootstocks resistant to telluric parasites would not have been inclined to search for a solution in the *C. baccatum* species, as the latter does not have resistance to the most threatening pathogens.

The second obstacle lies in the fact that the crossing between *C. annuum* and *C. baccatum* is considered by a person skilled in the art to be very difficult to perform, to such an extent that certain studies recommend the use of bridge species (or genotypes) in order to possibly succeed in crossing them (*C. chinense, C. annuum Turiabla*, etc.). Yoon J. B., 2009 (4) (Korea) describes the introgression of anthracnose resistance from *C. baccatum* to *C. annuum* by using *C. annuum* as the female parent in the initial crossing. The authors however describe the difficulty of the initial crossing and the sterility of the hybrid obtained. Egawa et al., 1986 (Japan) (5) explains the reason for the sterility of the interspecific hybrid resulting from the crossing of *C. annuum*×*C. baccatum* by the presence of at least three translocations between the two genomes. By succeeding in performing this crossing, the inventors overcame this obstacle and were able to introduce traits of agronomic interest, in particular resistance to telluric pathogens, from *C. annuum* to *C. baccatum*.

The invention is therefore based on a double advance: imagining that *C. baccatum* can serve as a rootstock in spite of the lack of resistance to the main telluric pathogens, and succeeding in introgressing at least one trait of agronomic interest, in particular resistance to a telluric pathogen, from *C. annuum* to *C. baccatum* even though the two species are considered to be incompatible.

The inventors in particular succeeded in crossing the *Capsicum annuum* and *Capsicum baccatum* plants.

In general, pepper cultivation, in particular in a rootstock, goes through a nursery step where the seeds are sown and germinated before being transferred to the field after around 50 to 70 days when they have reached a sufficient stage of development. For the nursery farmer, it is of utmost importance that all of the seeds sown germinate and develop normally, as each non-germinated seed takes up space that is unprofitable in the working greenhouse. By using a relatively undomesticated plant, such as *C. baccatum*, the risk of poor adaptation in the nursery (i.e. the risk of having a low germination percentage and/or non-uniform germination) are considered to be significant. However, to the inventors' surprise, it was found that the *C. baccatum* seeds used have satisfactory germination rates.

The balance between vegetative and generative development is normally difficult to achieve. Consequently, in the event of stress, as, for example under some intensive crop conditions, the generative activity takes over, resulting in good flowering but preventing the plant from growing and thus penalizing future harvests. It is then often necessary to wait for the fruits to fully mature on the plant or act by removing fruit in order to revitalize the crop and reactivate the vegetative activity, which ultimately leads to uneven productions. One of the reasons for this phenomenon, according to the authors of this invention, might arise from the weakness of the root system of *C. annuum*, which could not take over the vegetative and generative development at the same time.

*C. baccatum* appeared to the present inventors to be a valuable genetic resource in the problem of improving the traits of vigour and production of pepper rootstocks. In effect, *C. baccatum* has a more developed root volume than does *Capsicum annuum* and the inventors thought that a more powerful root volume could reduce the usual yield fluctuations of peppers.

Moreover, grafting is in particular intended to move the graft as far as possible from the soil pathogens. The graft must therefore take place as high as possible. It must also take place preferably under the cotyledons or possibly just above them in order to prevent the development of buds that might appear at the cotyledons and that the farmer would therefore have to remove during the production phase. The grafting therefore requires plants having a hypocotyl length that enables this result. The inventors showed that *C. baccatum* plants are particularly suitable because they have an average hypocotyl length greater than that of *C. annuum* plants. This hypocotyl length also facilitates the grafting since there is more room to work and perform the graft.

The inventors in particular successfully introduced, into *C. baccatum*, resistance to the soil parasites present in *C. annuum*, in particular resistance to *Phytophthora* and nematodes. To do so, the inventors performed multiple crossings between *C. baccatum* and *C. annuum* without an in vitro technique, and by using *C. baccatum* as the female parent during the initial crossing. It appears to be possible that the direction of the crossing might influence the success of the crossing.

The inventors thus came up with an original solution in the creation of new rootstock pepper plants wherein resistance to telluric diseases is combined with an improvement in vigour, by using, as the rootstock, not a *Capsicum annuum* plant but a *Capsicum baccatum* plant.

The rootstock plants according to the invention are plants obtained from crossings between plants of the *Capsicum* genus. The *Capsicum* genus belongs to the Solanaceae family and includes hot peppers and sweet peppers (or mild peppers). It includes in particular the species *Capsicum annuum, Capsicum baccatum, Capsicum buforum, Capsicum campylopodium, Capsicum cardenasii, Capsicum chacoense, Capsicum chinense, Capsicum coccineum, Capsicum cornutum, Capsicum dimorphum, Capsicum dusenii, Capsicum eximium, Capsicum flexuosum, Capsicum frutescens, Capsicum galapagoense, Capsicum geminifolium, Capsicum hookerianum, Capsicum lanceolatum, Capsicum leptopodum, Capsicum lycianthoides, Capsicum minutiflorum, Capsicum mirabile, Capsicum mositicum, Capsicum parvifolium, Capsicum pubescens, Capsicum rhomboideum, Capsicum schottianum, Capsicum scolnikianum, Capsicum tovarii* and *Capsicum villosum*. The most common species are *Capsicum annuum, Capsicum frutescens, Capsicum chinense, Capsicum pubescens* and *Capsicum baccatum*. The *Capsicum* genus has relatively significant physiological and genetic differences with respect to the other members of the Solanaceae family.

The *Capsicum annuum* species can be distinguished from the *Capsicum baccatum* species in particular in that the flowers of the *C. annuum* plants are white without yellow spots, while the white corolla of the flowers of *C. baccatum* plants has yellow spots.

A "chili pepper" or a "sweet pepper" is a plant of the *Capsicum* genus.

A "rootstock" or "rootstock plant" is a plant capable of receiving or having received a graft, i.e. a plant on which it is possible to implant a graft.

A "graft" is the part of a plant capable of being grafted onto a rootstock plant.

A "grafted plant" is the assembly formed by a "rootstock" and a "graft".

The *C. baccatum* rootstocks according to the invention have a more developed root volume and consequently make it possible to overcome the disadvantages of the existing *C. annuum* rootstocks, ensuring a more stable production of fruits and potentially a better yield for producers.

In addition, various *C. baccatum* accessions have already been described for resistance to *Fusarium* (6), *Verticillium* (7) and *Rhizoctonia* (8). It is also very likely that certain *C. baccatum* accessions have valuable behaviours (but not studied much as yet) with respect to soil fatigue, growth in cold and salinity, and possibly resistance to other diseases (*Ralstonia*, etc.). These traits may, of course, be highly valuable in a rootstock development program according to the invention.

According to a first embodiment, the present invention relates to a *Capsicum* plant suitable for use as a rootstock, capable of being obtained from the initial crossing of a *Capsicum* plant, preferably a *Capsicum annuum* plant, used as the male parent, with a *Capsicum baccatum* plant used as the female parent, wherein said *Capsicum* plant used as the male parent is different from said *Capsicum baccatum* plant used as the female parent. This initial crossing can be followed by at least one additional crossing with a *Capsicum baccatum* plant. Preferably, the initial crossing is followed by at least one, two, three, four, five, six, seven, eight or nine additional crossing(s) with a *Capsicum baccatum* plant. Preferably, said *Capsicum* plant used in the initial crossing is a *Capsicum annuum* plant.

According to an alternative embodiment, the present invention relates to a *Capsicum* plant suitable for use as a rootstock, capable of being obtained from the initial crossing of a *Capsicum* plant, preferably a *Capsicum annuum* plant, with a *Capsicum baccatum* plant, wherein said *Capsicum* plant is different from said first *Capsicum baccatum* plant, and wherein the initial crossing is followed by at least one additional crossing with a *Capsicum baccatum* plant. Preferably, the initial crossing is followed by at least one, two, three, four, five, six, seven, eight or nine additional crossing(s) with a *Capsicum baccatum* plant. Preferably, in the initial crossing, the *Capsicum baccatum* plant is used as the female parent. Also preferably, said *Capsicum* plant used in the initial crossing is a *Capsicum annuum* plant.

For the implementation of one or the other of the above methods enabling rootstock plants according to the invention to be obtained, each additional crossing can be performed with a *Capsicum baccatum* identical to that used during the initial crossing (this is called backcrossing) or with a different plant.

For example, for the implementation of one or the other of the above methods enabling the rootstock plants according to the invention to be obtained, the initial crossing is followed by three or four additional crossings with a *Capsicum baccatum* plant identical to that used in the initial crossing (backcrossing) or with a different plant.

According to a particular embodiment, the *Capsicum baccatum* plant used in at least one, preferably one, two, three or four additional crossing(s) is identical to the *Capsicum baccatum* plant used in the initial crossing (backcrossings). This implementation makes it possible in particular to more quickly obtain a rootstock plant having a stable *C. baccatum* phenotype.

In the initial crossing or additional crossings (or backcrossings), in particular when they are interspecific (for example a crossing between *C. annuum* and *C. baccatum* or a backcrossing of the plant obtained with *C. baccatum*), the use of an in vitro technique such as embryo or ovary culture may be necessary according to the genotypes of the two parents, in order to perform a crossing or increase the efficacy of same. These techniques are well known to a person skilled in the art and are, for example, illustrated in Dumas de Vaulx, 1992 (9).

According to a particular embodiment, an in vitro technique is not used during the initial crossing, in particular when the female parent is the *C. baccatum* plant.

"Identical" plants are plants not capable of being distinguished genotypically or phenotypically. For example, they may be plants obtained from the same stabilized population or plants of the same variety or line.

According to a preferred implementation of one or the other of the above methods enabling the rootstock plants according to the invention to be obtained, the *Capsicum baccatum* used in at least one, preferably, one, two, three or four additional crossing(s) is different from the *Capsicum baccatum* plant used in the initial crossing. This implementation is particularly advantageous insofar as it makes it possible to combine, in the rootstock plant, traits of interest from two *Capsicum baccatum* plants having a different genetic heritage. The second *C. baccatum* may, for example, be the *C. baccatum* plant registered under accession number PBC1405 (AVRDC, 2000).

"Different" plants are, in particular, plants capable of being distinguished genotypically or phenotypically. For example, they may be plants obtained from different populations, plants of different species, plants of different varieties or lines or plants differing by at least one trait of agronomic interest.

According to a particular embodiment, all of the additional crossings are performed with *Capsicum baccatum* plants identical to one another and they may or may not be identical to the plant used in the initial crossing.

According to an advantageous embodiment, all of the additional crossings are not performed with *Capsicum baccatum* plants identical to one another. Preferably, the first additional crossing(s) is (are) performed with a *C. baccatum* plant identical to the *C. baccatum* plant used in the initial crossing, preferably until the phenotype of the plant is stabilized, and the subsequent additional crossing(s) are performed with a *C. baccatum* plant different from the *C. baccatum* plant used in the initial crossing. The plant obtained then has a hybrid character between different *C. baccatum* plants or accessions. According to a preferred implementation of one or the other of the above methods making it possible to obtain the rootstock plants according to the invention, the *Capsicum* plant used in the initial crossing is a *Capsicum annuum* plant and comprises at least one trait of agronomic interest, and each of the crossings or backcrossings is followed by a step of selecting plants comprising said trait(s) of agronomic interest.

A "trait of agronomic interest" is an agronomically or agriculturally valuable trait of a cultivated plant, in particular a trait making it possible to facilitate or accelerate the cultivation of the plant or a trait conferring an improved quality on the plant. It may be, in particular, resistance to a pathogen, in particular a telluric pathogen, the volume and quality of the root system, the hypocotyl length, the hybrid vigour, the homeostasis, the capacity for adaptation to abiotic stress, in particular adaptation to a high-lime soil, a hydromorphic soil, a cold soil, root asphyxiation, a lack of water or saline stress, the absence or presence of male sterility, a morphological characteristic such as colour, the shape of the seeds or the fruits, the softness or rigidity of the leaves, the nutrient composition or a gustatory characteristic of the fruits or the plant.

Preferably, the *Capsicum* plant used in the initial crossing is a *Capsicum annuum* plant and comprises at least two traits of agronomic interest, and each crossing or backcrossing is followed by a step of selecting plants comprising said traits of agronomic interest.

According to a particularly preferred implementation, the trait(s) of agronomic interest of the *C. annuum* plant is (are) resistance to pathogens, and in particular resistance to telluric pathogens. Preferably, said resistance is chosen from resistances to *Ralstonia solanacearum, Rhizoctonia solani, Pythium* spp., *Fusarium oxysporum, Phytophthora capsici, Sclerotium rolfsii, Verticillium albo-atrum, Verticillium dahliae, Meloidogyne incognita, Meloidogyne arenaria, Meloidogyne javanica, Meloidogyne hapla, Meloidogyne enterolobii* and PMMV, TMV, TSWV or PVY viruses. Particularly preferably, said resistance is chosen from resistances to *Phytophthora capsici, Meloidogyne incognita, Meloidogyne javanica* and *Meloidogyne arenaria*. It may, for example, be resistance to *Phytophthora* and to nematodes of the *Capsicum annuum* plant registered under accession number CM334 (INRA).

Particularly preferably, the *Capsicum annuum* plant is a *Capsicum annuum* plant comprising resistance, in particular intermediate resistance to *Phytophthora* and resistance, in particular intermediate resistance to *Meloidogyne*.

A "pathogen" is a biological agent responsible for an infectious disease in a plant and more specifically in the pepper. It may more particularly refer to animals such as insects or nematodes, fungi, parasites, bacteria or viruses.

A "telluric pathogen" is a pathogen that lives in the soil.

The main telluric pathogens attacking the pepper are *Phytophthora capsici, Rhizoctonia solani* and *Fusarium solani*, and the root-knot nematodes or *Meloidogyne* spp. (*Meloidogyne incognita, Meloidogyne arenaria, Meloidogyne javanica* and *Meloidogyne hapla*):

*Phytophthora capsici* Leonian is a telluric pathogen (soil fungus) causing the disappearance of pepper plants and plantlets, which wither and die from root rot and crown rot. The pathogen's attack may also be manifested on the fruits with small brown spots around 1 mm in diameter, which grow and cause deeper lesions. Zoospores may spread by splashing from the contamination sites. The current treatments are based on limiting the watering of plants and using more or less resistant cultivars.

*Rhizoctonia solani* is a telluric pathogen (soil fungus) found throughout the world and of which the pepper is one of many plant hosts. The diseases caused by this fungus have various names: black scurf, sheath blight, black leg, seedling blight or damping off, crater rot, web blight, parasitic lodging, crown rot, etc. For example, in seedling blight, the roots rot and cause death in patches. *Rhizoctonia* specific to market gardening crops are virulent, especially in colder soils, without stagnant humidity and cause significant and costly yield losses.

*Fusarium solani*, also called *fusarium* rot of the stem and fruits, causes significant plant and fruit yield losses. It is often found in combination with *Rhizoctonia solani*. *Fusarium solani* can attack a wide range of plants, including greenhouse vegetables. In the pepper, the symptoms are soft, dark brown or black cankers on the stem, generally at the level of the nodes or wounds, even capable of surrounding the stem in the final stages of the disease. A dark brown spot colours the interior of the stem and may extend over a considerable length. At the surface of the stem cankers, in the final stages of the disease, it is also possible to observe the presence of mycelium, a white cottony mass, which represents the imperfect stage of the fungus. The stem cankers impede the upward passage of water in the plant, which, poorly irrigated, eventually withers and dies. The fruits may also be subject to the *Fusarium solani* attack, and develop aqueous black spots that grow, merge and cover the surfaces of the fruits. Mycelium develops abundantly when the greenhouse environment is very humid, and in particular when the temperature exceeds 25° C.

*Meloidogyne incognita* is a nematode, a type of roundworm of the Heteroderidae family. The nematodes of the *Meloidogyne* genus cause the appearance of round scabs, or even swelling on the roots. These lesions cause withering and slowing of growth. Nematodes are polyphagous and attack numerous vegetable crops such as tomatoes, lettuce, aubergine and peppers.

The concepts of "resistance", "immunity" and "susceptibility" are defined by the ISF (International Seed Federation)".

Thus, "resistance" refers to the capacity of a plant or a variety to limit the growth and development of a determined pathogen or pest and/or the damage that they cause, by comparison with susceptible varieties and under similar environmental and pressure conditions of said pathogen or pest. Resistant plants or varieties may express some symptoms of the disease or some damage under high pressure of the pathogen or the pest.

The ISF distinguishes two levels of resistance, namely standard resistance or high resistance (HR*) and intermediate or moderate resistance (IR*).

"Standard or high resistance (HR*)" refers to the capacity of a plant or a variety to significantly limit the growth and development of a determined pathogen or pest under normal pressure conditions of said pathogen or pest, by comparison with susceptible varieties. These plants or varieties may, however, express symptoms or damage under high pressure of said pathogen or pest.

"Intermediate or moderate resistance (IR*)" or "partial resistance" refers to the capacity (HR*) of the variety to limit the growth and development of a determined pathogen or pest, but which may express more symptoms or damage by comparison with varieties with high/standard resistance. The plants or varieties with intermediate resistance will show less severe symptoms or damage than those observed on susceptible varieties, under similar environmental and/or pressure conditions of the pathogen or pest.

"Immunity" means not being subject to attack or infection by a given pest or pathogen.

"Susceptibility" refers to the inability of a plant or a variety to limit the growth or development of a determined pathogen or pest.

According to a preferred embodiment of one or the other of the above methods enabling rootstock plants according to the invention to be obtained, the *Capsicum baccatum* plant(s) used in crossing(s) comprise at least one, preferably at least two, trait(s) of agronomic interest, and each of said crossings is followed by a step of selecting plants comprising said trait(s) of agronomic interest. Particularly preferably, the *Capsicum baccatum* plant(s) has (have), at a given crop stage, for example, six to twelve months after germination, a root volume, a root mass and/or a hypocotyl height that is 10%, and preferably 20%, 30%, 40% or 50% greater than those of the TECNICO variety at the same stage, cultivated under identical conditions.

Figure 2:
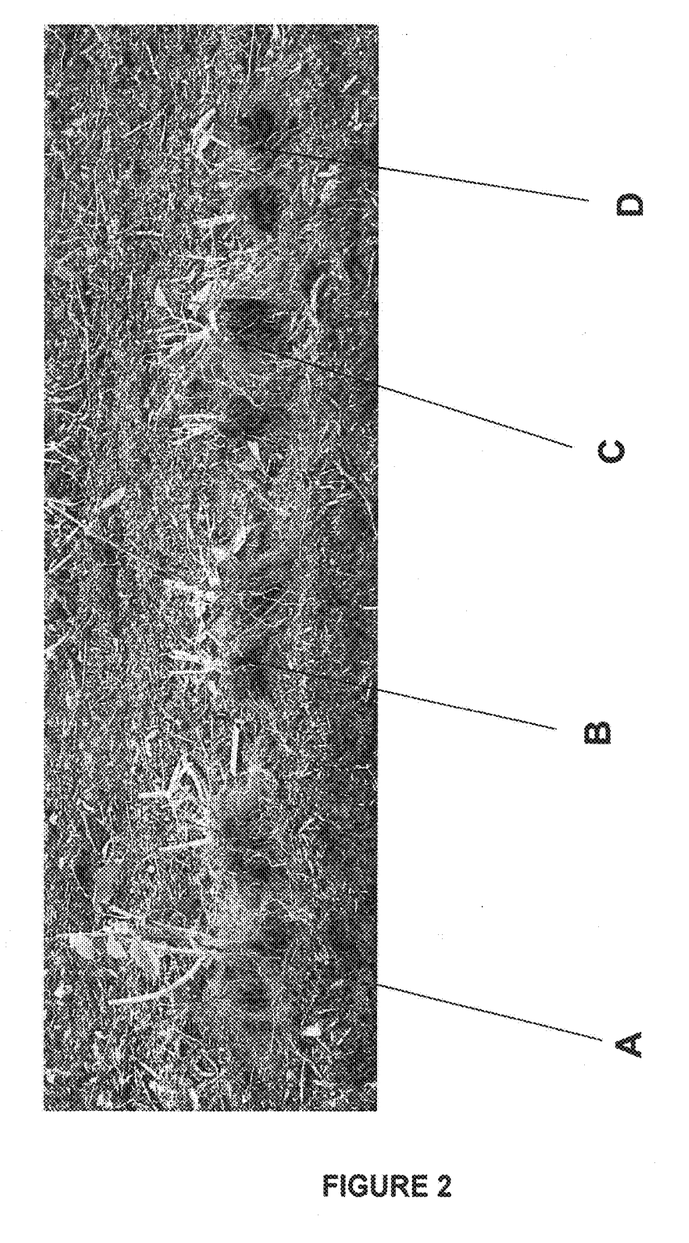
FIG. 2—Root volume and architecture of non-grafted plants
Figure 3A:
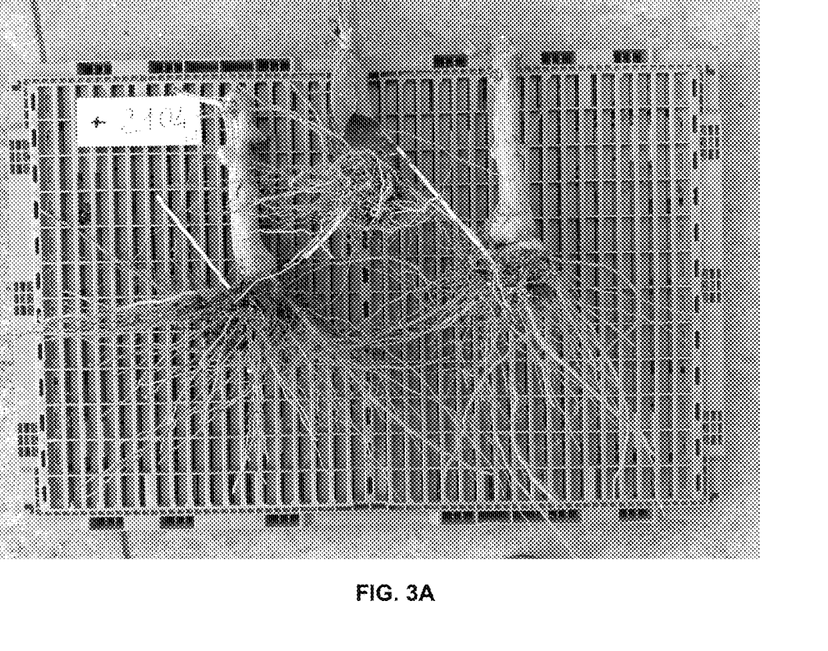
FIG. 3A-3E—Root volume and architecture of grafted plants (trial 2)
Figure 3B:
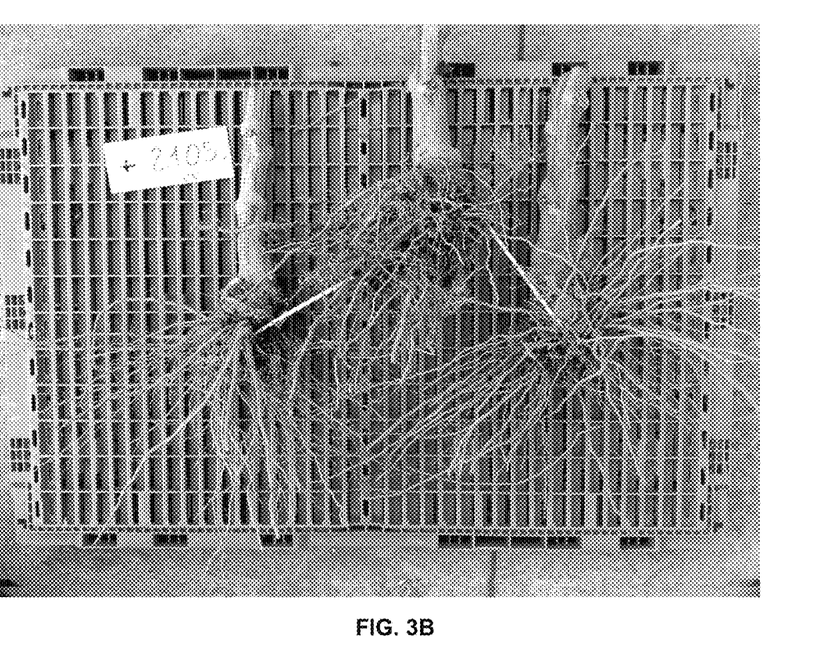
Figure 3C:
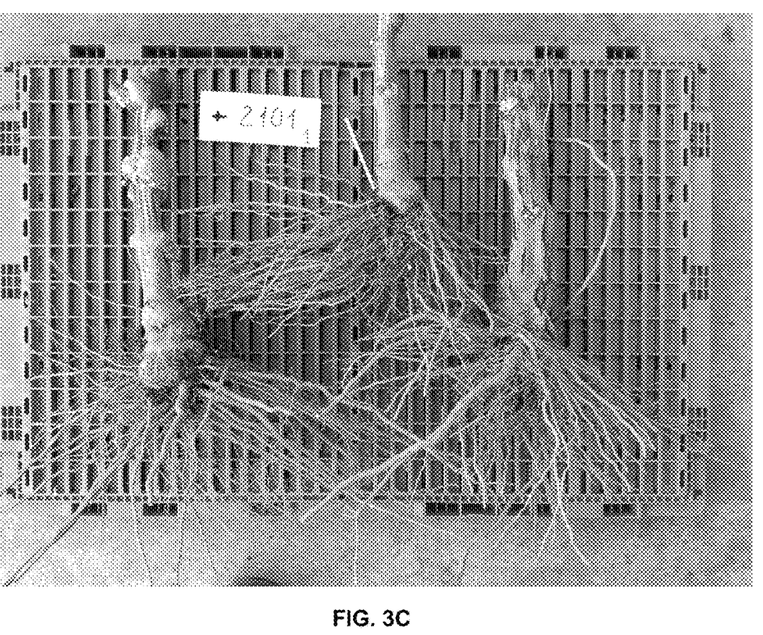
Figure 3D:
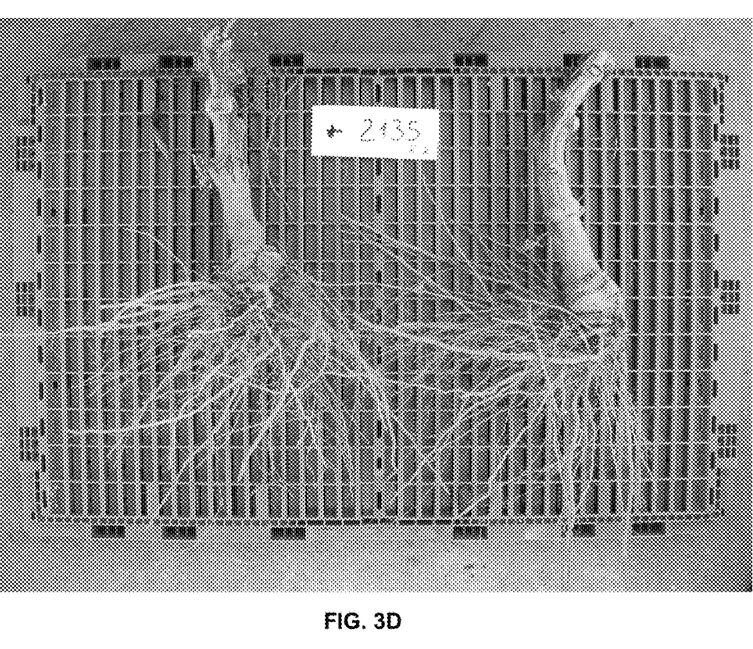
Figure 3E:
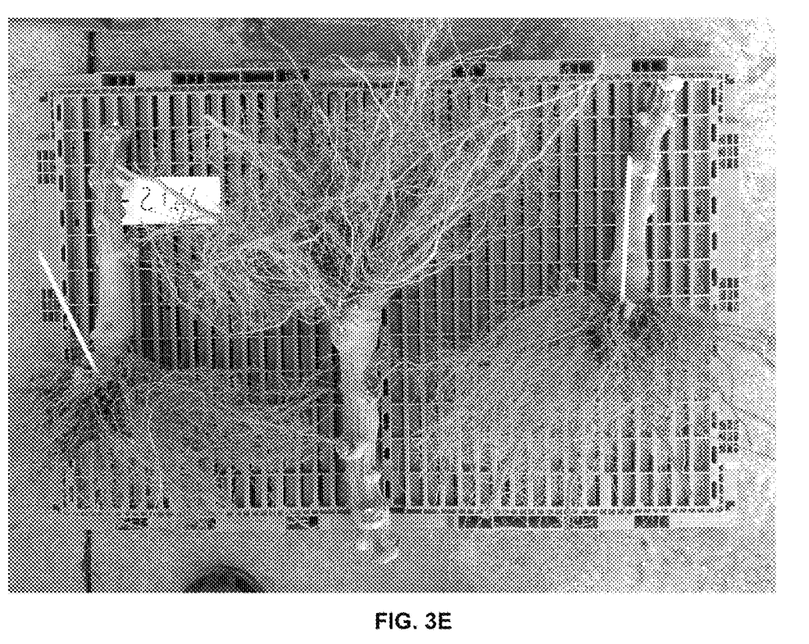

The "root volume" of a given plant or variety can be estimated in particular according to the number and length of the roots. It is subject to variation in particular according to the soil composition and meteorological conditions, but it varies in the same proportions from one plant to another. A scale of 1 to 5 (1=very low; 2=low; 3=moderate; 4=developed; 5=highly developed) may be used to characterize the root volume. FIG. 2 shows this scale. The root volume may also be estimated by comparing the length and/or the number of roots of the plant studied and a reference *Capsicum* plant cultivated under the same conditions. The reference *Capsicum* plant may, for example, be a plant of the SNOOKER variety, or a plant of the TECNICO variety, having been the subject of a seed deposit on 2 Mar. 2011 with the NCIMB (NCIMB Ltd., Ferguson Building, Craibstone Estate, Bucksburn, Aberdeen, AB21 9YA, Scotland, United Kingdom) under accession number NCIMB 41815. The TECNICO variety is a *Capsicum annuum* F1 hybrid.

The "root architecture" (or "root structure") of a given plant or variety can be estimated in particular according to the more or less significant presence of root "hair", i.e. the amount, weight and/or volume of small root branches originating from the main roots. It is subject to variation in particular according to the soil composition and meteorological conditions, but it varies in the same proportions from one plant to another. A scale of 1 to 5 (1=very low; 2=low; 3=moderate; 4=developed; 5=highly developed) may be used to characterize the root volume. FIG. 2 shows this scale. The root architecture may also be estimated by comparing the weight of the roots of the plant studied and a reference *Capsicum* plant cultivated under the same conditions. The reference *Capsicum* plant may, for example, be a plant of the SNOOKER variety, or a plant of the TECNICO variety.

The "hypocotyl" is the part of the stem of a plant located between the base of the stem and the first cotyledons. The length of the hypocotyl is subject to variation in particular according to the soil composition and meteorological conditions, but it varies in the same proportions from one plant to another. The length of the hypocotyl of the plant studied can be compared to that of a reference *Capsicum* plant cultivated under the same conditions. The reference *Capsicum* plant may, for example, be a plant of the SNOOKER variety, or a plant of the TECNICO variety.

Preferably, the rootstock plant according to the invention has one or more traits of agronomic interest chosen from resistance to a pathogen, in particular intermediate or standard resistance to a telluric pathogen, a root volume at a given crop stage that is 10%, and preferably 20%, 30%, 40% or 50% greater than those of the TECNICO variety at the same stage and cultivated under identical conditions, a root mass at a given crop stage that is 10%, and preferably 20%, 30%, 40% or 50% greater than those of the TECNICO variety at the same stage and cultivated under identical conditions and a hypocotyl height at a given crop stage that is 10%, and preferably 20%, 30%, 40% or 50% greater than those of the TECNICO variety at the same stage and cultivated under identical conditions, the homeostasis, tolerance to a high-lime soil or the capacity for adaptation to an abiotic stress, in particular adaptation to a high-lime soil, a hydromorphic soil, a cold soil, root asphyxiation, a lack of water or saline stress.

The crop stage at which the root volume, root mass or hypocotyl height is measured is preferably the "end of crop" stage, i.e. the stage of maximum development of the plant, generally reached six to twelve months after germination, after harvesting of the fruits and before pulling up the plant.

"Heterosis" or "hybrid vigour" refers to the phenomenon according to which an F1 hybrid is significantly greater than the best of its parents with regard to one or more traits, in particular with regard to vigour.

"Homeostasis" refers to the capacity of a plant to adapt to different environments.

Advantageously, the rootstock plant according to the invention comprises at least two traits of agronomic interest. Particularly preferably, the rootstock plant according to the invention comprises at least two traits of agronomic interest, of which at least one is resistance to a telluric pathogen.

Preferably, the rootstock plant according to the invention is resistant to at least one or at least two pathogens, in particular chosen from *Ralstonia solanacearum*, *Rhizoctonia solani*, *Pythium* spp., *Fusarium oxysporum*, *Phytophthora capsici*, *Sclerotium rolfsii*, *Verticillium alboatrum*, *Verticillium dahliae*, *Meloidogyne incognita*, *Meloidogyne arenaria*, *Meloidogyne javanica*, *Meloidogyne hapla*, *Meloidogyne enterolobii* and the PMMV, TMV, TSWV or PVY viruses. Particularly preferably, said resistances are chosen from resistances to *Phytophthora capsici*, *Meloidogyne incognita*, *Meloidogyne javanica* and *Meloidogyne arenaria*. According to a preferred embodiment, the resistance(s) stem from the initial parent *Capsicum annuum*. According to a particularly preferred embodiment, the rootstock plant according to the invention has resistance to

*Phytophthora capsici* and resistance to *Meloidogyne*. According to a particular embodiment, it is intermediate resistance.

Also preferably, the rootstock plant according to the invention also comprises at least one or at least two traits of agronomic interest other than resistances. Particularly preferably, it is a root volume at a given crop stage that is 10%, and preferably 20%, 30%, 40% or 50% greater than that of the TENICO variety at the same stage and cultivated under identical conditions, a root mass at a given crop stage that is 10%, and preferably 20%, 30%, 40% or 50% greater than that of the TENICO variety at the same stage and cultivated under identical conditions, and/or a hypocotyl height at a given crop stage that is 10%, and preferably 20%, 30%, 40% or 50% greater than that of the TENICO variety at the same stage and cultivated under identical conditions. According to a preferred implementation, these traits other than resistance are obtained from the *Capsicum baccatum* parents.

Particularly preferably, the rootstock plant according to the invention comprises at least one or at least two standard or intermediate resistances to telluric pathogens, in particular chosen from resistances to *Phytophthora capsici, Meloidogyne incognita, Meloidogyne javanica* and *Meloidogyne arenaria*, and at least one or at least two traits of agronomic interest other than resistance, in particular a root volume at a given crop stage that is 10%, and preferably 20%, 30%, 40% or 50% greater than that of the TENICO variety at the same stage and cultivated under identical conditions, a root mass at a given crop stage that is 10%, and preferably 20%, 30%, 40% or 50% greater than that of the TENICO variety at the same stage and cultivated under identical conditions, and/or a hypocotyl height at a given crop stage that is 10%, and preferably 20%, 30%, 40% or 50% greater than that of the TENICO variety at the same stage and cultivated under identical conditions.

The present invention relates in particular to a *Capsicum baccatum* plant suitable for use as a rootstock, comprising resistance to *Phytophthora* capsici and resistance to *Meloidogynes*. According to a preferred embodiment, it is intermediate resistance. According to a preferred implementation, the partial resistance to *Phytophthora capsici* is conferred by the P5 gene from *C. annuum* and the partial resistance to *Meloidogynes* is conferred by the Me7 gene from *C. annuum*. According to a particular implementation, these two resistance genes come from the *C. annuum* variety CM334 (INRA). Preferably, the *C. capsicum* plant according to the invention has a root volume at a given crop stage that is 10%, and preferably 20%, 30%, 40% or 50% greater than that of the TENICO variety at the same stage and cultivated under identical conditions, a root mass at a given crop stage that is 10%, and preferably 20%, 30%, 40% or 50% greater than that of the TENICO variety at the same stage and cultivated under identical conditions, and/or a hypocotyl height at a given crop stage that is 10%, and preferably 20%, 30%, 40% or 50% greater than that of the TENICO variety at the same stage and cultivated under identical conditions.

The methods for breeding and selecting plants having a trait of agronomic interest are well known to a person skilled in the art. In particular, they are methods based on phenotypic observations, comparison with reference lines or detection of molecular markers.

The resistances can in particular be detected after inoculation with the pathogenic agent and/or cultivation in a contaminated field by phenotypic observations or by molecular markers.

The present invention also relates to grafted plants. The grafted plants according to the invention consist of a rootstock plant obtained by crossing plants of the *Capsicum* genus, and a graft.

In particular, a grafted plant according to the invention consists of a rootstock and a graft, wherein said rootstock is a plant obtained by an initial crossing of a *Capsicum* plant with a *Capsicum baccatum* plant, said *Capsicum* plant being different from said *Capsicum baccatum* plant, and wherein the initial crossing is optionally followed by at least one, and preferably one to six, additional crossing(s) with a *Capsicum baccatum* plant. Preferably, the first *Capsicum* plant is a *Capsicum annuum* plant. According to another implementation, it is a *Capsicum baccatum* plant.

The grafting techniques suitable for grafting on a rootstock pepper are well known to a person skilled in the art. In a non-limiting manner, it is possible to cite the Japanese graft, the approach graft, the cleft graft and the whip and tongue graft.

The Japanese graft is the technique most commonly used. It is performed just below the cotyledons (bottom graft) or below the first leaf (top graft). The graft and the rootstock are sectioned on an angle at the chosen level and are placed in contact and held by means of a small silicone ring. It is important for the diameter of the graft and that of the rootstock to be identical or partially identical (around 1.5 mm) in order to ensure a good take of the grafted plant. This ring will not impede the subsequent growth of the stem.

In particular, care should be taken to ensure that there is a good match between the graft and the rootstock with precautions taken starting with the grafting by choosing identical or almost identical stem diameters so that the junction between the tissues is correct, and thus ensure the take of the rootstock/graft assembly.

Preferably, the rootstock is a rootstock plant according to the invention.

Preferably, the graft is a plant of the *Capsicum* genus. Particularly preferably, the graft is a plant of the *Capsicum annuum, Capsicum frutescens* or *Capsicum chinense* species.

The present invention also relates to a seed from a rootstock plant according to the invention.

The present invention also relates to a cell from a rootstock plant or a grafted plant according to the invention.

The present invention also relates to a part of a rootstock plant or a grafted plant according to the invention.

The present invention also relates to the use, as a rootstock of a plant obtained from the initial crossing of a *Capsicum* plant, preferably a *Capsicum annuum* plant, with a *Capsicum baccatum* plant, wherein said *Capsicum* plant is different from said *Capsicum baccatum* plant, and wherein the initial crossing is optionally followed by at least one, two, three, four, five, six, seven, eight or nine additional crossing(s) with a *Capsicum baccatum* plant. Advantageously, the plant used as the rootstock is a rootstock plant according to the invention. Preferably, the rootstock plant is associated with a graft of the *Capsicum* genus, and particularly preferably with a graft of the *Capsicum annuum, Capsicum frutescens* or *Capsicum chinense* species.

The present invention also relates to a method for obtaining a grafted plant including the grafting of a graft on a rootstock plant, wherein said rootstock plant is obtained by crossing a *Capsicum* plant, preferably a *Capsicum annuum* plant, with a *Capsicum baccatum* plant, said *Capsicum* plant being different from said *Capsicum baccatum* plant, and wherein the initial crossing is optionally followed by at least one, two, three, four, five, six, seven, eight or nine additional crossing(s) with a *Capsicum baccatum* plant.

Advantageously, the plant used as the rootstock is a plant according to the invention. Preferably, the plant used as the graft is a plant of the *Capsicum* genus, in particular a plant of the *Capsicum annuum, Capsicum frutescens* or *Capsicum chinense* species.

FIGURES

A—*Capsicum annuum* flower (origin: Central America, root weakness, resistance to *Phytophthora* and nematodes)

B—*Capsicum baccatum* flower (origin: Amazon Basin, root strength (R asphyxiation), possible resistance to *Verticillium* and *Ralstonia*)

C—Result of hybridization between *C. annuum* and *C. baccatum*. Crossings between *C. annuum* and about one hundred accessions of *C. baccatum* were produced, twenty hybrids were harvested and seven hybrids were verified (including by marking). On the left: flower of the *C. annuum* male parent (hairy plant and white flower); on the right: flower of the *C. baccatum* female parent (glabrous plant and flower with spot); in the centre, flower of the F1 hybrid obtained by crossing two parents (slightly hairy plant and flower with light spots).

A—*C. baccatum*\*PBC1405 hybrid: root volume=5

B—*C. annuum* TECNICO control: root volume=2

C—*C. annuum* SNOOKER control: root volume=2

D—*C. annuum* TRESOR control: root volume=1

3A—SNOOKER rootstock: root volume=2; root architecture=2

3B—TRESOR rootstock: root volume=2; root architecture=1

3C—TECNICO rootstock: root volume=3; root architecture=2

3D—ROBUSTO rootstock: root volume=4; root architecture=2

3E—Rootstock obtained from crossing PI 413669 01 SD\*PBC1405: root volume=5; root architecture=5.

EXPERIMENTAL PART

1. Selection and Use of *C. baccatum* Plants as Rootstocks

The inventors performed three sequential steps.

First, they identified, outside of the *C. annuum* species, within the *C. baccatum* species, genetic resources making it possible to improve the productivity of the current rootstocks, in particular according to their significant root vigour.

They then confirmed that these resources had valuable behaviours with regard to grafting sites (good germination and sufficient hypocotyl length).

The inventors finally formed a grafted plant using a *C. baccatum* rootstock, in particular hybrid rootstocks utilizing the heterosis between different *C. baccatum* accessions and having valuable characteristics in the nursery (good germination and hypocotyl length) and in cultivation (gain in vigour and productivity).

It should be noted that the improvement in the *C. baccatum* hybrid plant according to the third step may be optional, according to characteristics already present in the *C. baccatum* plant chosen as the rootstock. Indeed, while, in general, one may expect that the rootstock is preferably a hybrid plant obtained by crossing two *C. baccatum* lines utilizing heterosis, it cannot be denied that a baccatum plant line has enough traits of interest to, alone, be an acceptable rootstock.

First, the inventors identified, from a representative collection of *C. baccatum* plants, the best accessions in inherent value and in hybrid form on the basis of their behaviour in the nursery and in the field, with or without grafting according to the following: root development, vigour of the grafted plant, germination, vigour and height of the plant in the nursery.

The results presented below relate to four grafting trials performed over two consecutive years and in two different locations.

1.1 Comparison of the Root Volume of *C. annuum* and *C. baccatum* Plants

The inventors compared the root volume of six different *C. annuum* control plants with that of 90 different *C. baccatum* plants, under identical culture conditions, using a scale ranging from 1 (very weak) to 5 (highly developed).

The planting was performed in mid-May and the evaluation of the root volume was performed at the beginning of November.

The results are presented in table 1 and show that the average root volume of the *C. baccatum* plants is 4.2, i.e. on average two times greater than that of the *C. annuum* control plants (2.1). The root volume of an HF-1 hybrid obtained by crossing accessions USDA PI 413669 01 and PBC1405 was also determined to be equal to 4.

The roots of some of the plants obtained are presented in FIG. 2.

TABLE 1

| Root volume | | |
|---|---|---|
| Plants (not grafted) | Number | Root volume |
| *C. annuum* (average) | 6 | 2.1 |
| *C. baccatum* (average) | 90 | 4.2 |
| PG-TRESOR *C. annuum* | | 1.0 |
| PG-SNOOKER *C. annuum* | | 2.0 |
| TECNICO *C. annuum* | | 2.0 |
| USDA PI 413669 01 \* PBC1405 (HF1) *C. baccatum* | | 4.0 |

Root volume: 1 = very weak; 2 = weak; 3 = average; 4 = developed; 5 = highly developed 1.2 Behaviour in the Nursery Prior to the grafting, the inventors compared the germination percentage in the nursery and the hypocotyl length just before grafting different *C. annuum* plants, with that of plants obtained from crossing different *C. baccatum* accessions with the *C. baccatum* accession PBC1405.

The results are presented in table 2 and show that the *C. baccatum* seeds have satisfactory germinations, their average germination percentage even being greater than that of the *C. annuum* plants. This result is unexpected insofar as, with relatively undomesticated plants, the risk of poor germination is considered to be high.

The hypocotyl length of the *C. baccatum* plants is greater than that of the *C. annuum* plants. This characteristic is particularly advantageous in the context of use as a rootstock.

TABLE 2

Germination percentage and hypocotyl length

| Trial | Plant | Number | % Germination | Hypocotyl length (in mm) |
|---|---|---|---|---|
| Trial 1 | C. annuum (average) | 30 | — | 30.4 |
| | C. baccatum (average) | 18 | — | 37.3 |
| | PG-TRESOR C. annuum | | — | 29 |
| | PG-SNOOKER C. annuum | | | 37 |
| | TECNICO C. annuum | | | 34 |
| | USDA PI 413669 01 SD*PBC1405 C. baccatum | | | 37 |
| Trial 2 | C. annuum (average) | 28 | 78% | 21.3 |
| | C. baccatum (average) | 15 | 80% | 29.9 |
| | PG-TRESOR C. annuum | | 80% | 23.3 |
| | PG-SNOOKER C. annuum | | 90% | 28 |
| | ROBUSTO C. annuum | | 72% | 17.7 |
| | TECNICO C. annuum | | 60% | 26.5 |
| | USDA PI 413669 01 SD*PBC1405 C. baccatum | | 100% | 33.9 |
| Trial 3 | C. annuum (average) | 56 | 77% | 29.2 |
| | C. baccatum (average) | 35 | 75% | 31.5 |
| | PG-TRESOR C. annuum | | 100% | 27 |
| | PG-SNOOKER C. annuum | | 80% | 31 |
| | TECNICO C. annuum | | 100% | 27 |
| | USDA PI 413669 01 SD*PBC1405 C. baccatum | | 100% | 35.4 |
| Trial 4 | C. annuum (average) | 28 | 73% | 26.3 |
| | C. baccatum (average) | 19 | 82% | 34.1 |
| | PG-TRESOR C. annuum | | 96% | 30 |
| | PG-SNOOKER C. annuum | | 72% | 29.5 |
| | ROBUSTO C. annuum | | 68% | 19.8 |
| | TECNICO C. annuum | | 94% | 26.4 |
| | USDA PI 413669 01 SD*PBC1405 C. baccatum | | 96% | 35.5 |

1.3 Obtaining Grafted Plants

The inventors grafted a C. annuum plant on different C. annuum rootstock plants and different C. baccatum rootstock plants obtained from crossings. The same C. annuum graft, Eppo, was used for all of the grafted plants. The graft technique used is the Japanese graft.

The characteristics of the grafted plants were then determined. The results are presented in table 3. The roots of the plants of trial 2 are presented in FIGS. 3A-3E.

The grades for vigour and early fruiting make it possible to determine whether the growth of the plant is balanced, i.e. if the balance between vegetative and generative development is respected. A low earliness grade indicates excessive vegetative development, while a low vigour grade indicates excessive generative development. The ideal is to have high earliness (good fruiting) with high vigour. The results obtained show that there was no imbalance after grafting, even though this is often the case during grafting with a C. annuum rootstock (excessively generative) and there is a risk of obtaining an excessively vegetative grafted plant due to the use of a highly vigorous rootstock plant.

The affinity grade characterizes the quality of the junction (connection of vessels, etc.) between the stem of the graft and that of the rootstock. A high grade corresponds to a good alignment and an absence of enlargement at the graft point. The results obtained show that the compatibility between the C. annuum graft and the C. baccatum rootstocks is approximately the same as that of the graft with the C. annuum rootstocks.

The grades for root volume and extent of root hair make it possible to evaluate the quality of the root system. The results obtained show that the root system of the grafted plants for which the rootstocks are C. baccatum plants is significantly superior to that of the plants grafted using C. annuum rootstocks. Consequently, the use of C. baccatum rootstocks makes it possible to obtain grafted plants of which the root system is more developed and denser, thereby allowing for improved productivity.

TABLE 3

Characteristics of grafted plants

| Trial | Plant | Number | Earlines | Vigour | Affinity | Root Vol. | Root cap. |
|---|---|---|---|---|---|---|---|
| Trial 1 | C. annuum (average) | 30 | 3.1 | 3.2 | — | — | — |
| | C. baccatum (average) | 18 | 4.0 | 3.0 | — | — | — |
| | PG-SNOOKER C. annuum | | 3.0 | 3.8 | — | — | — |
| | PG-TRESOR C. annuum | | 3.0 | 3.2 | — | — | — |
| | TECNICO C. annuum | | 2.5 | 2.8 | — | — | — |
| | USDA PI 413669 01 SD*PBC1405 C. baccatum | | 4.0 | 3.8 | — | — | — |
| Trial 2 | C. annuum (average) | 28 | 3.1 | 3.4 | 2.3 | 3.0 | 2.5 |
| | C. baccatum (average) | 14 | 3.5 | 3.6 | 3.1 | 3.7 | 4.1 |
| | PG-SNOOKER C. annuum | | 4.0 | 3.8 | 2.8 | 2.0 | 2.0 |
| | PG-TRESOR C. annuum | | 3.3 | 3.5 | 3.0 | 2.0 | 1.0 |
| | ROBUSTO C. annuum | | 3.0 | 3.3 | 2.0 | 4.0 | 2.0 |
| | TECNICO C. annuum | | 3.5 | 3.3 | 3.5 | 3.0 | 2.0 |
| | USDA PI 413669 01 SD*PBC1405 C. baccatum | | 3.3 | 4.3 | 4.0 | 5.0 | 5.0 |
| Trial 4 | C. annuum (average) | 28 | 2.7 | 3.4 | 3.5 | 3.7 | 3.6 |
| | C. baccatum (average) | 19 | 2.5 | 3.2 | 2.5 | 4.0 | 3.8 |
| | PG-SNOOKER C. annuum | | 3.0 | 2.8 | 3.5 | 3.0 | 2.5 |
| | PG-TRESOR C. annuum | | 1.5 | 3.7 | 4.0 | 3.5 | 3.5 |
| | ROBUSTO C. annuum | | 3.5 | 2.8 | 3.5 | 2.0 | 3.0 |
| | TECNICO C. annuum | | 2.2 | 3.2 | 4.2 | 4.2 | 4.0 |
| | USDA PI 413669 01 SD*PBC1405 C. baccatum | | 3.0 | 2.7 | 3.0 | 4.0 | 5.0 |

Earliness: early fruiting or setting; vigour: aerial development of the plant (foliar mass); affinity: quality of the junction between the graft and the rootstock; root vol.: root volume; root cap.: extent of root hair (root mass); 1 = very low; 2 = low; 3 = medium; 4 = high; 5 = very high

2. Transfer of Resistance from *C. annuum* to *C. baccatum*

Two crossings were performed between the accessions of *C. annuum* CM334 comprising genes with P5 resistance (partial resistance to *Phytophthora*) and Mel (partial resistance to nematodes), and *C. baccatum* PBC1405. For the first crossing, the female parent was the accession PBC1405 and for the second crossing, the female parent was the accession CM334. The first crossing resulted in the presence of fruit, but the second did not.

The inventors chose to use the *C. annuum* accession CM334 as the male parent and crossed it in a conventional manner with 95 different *C. baccatum* accessions used as the female parents.

The presence of fruit after hybridization, the presence of seeds in the hybridized fruit and the number of seeds harvested by crossing were then determined. A maximum of 10 seeds were then sown for each crossing having enabled the seed harvest. The capacity of sown F1 (HF1) hybrid seeds leading to germination and the number of F1 hybrid plants obtained were also determined. Of the 95 crossings performed, 46 resulted in fruit, 24 enabled hybrid seeds to be obtained, and the seeds from 10 of these crossings led to germination. These results confirm that it is possible, without using an in vitro technique, to obtain F1 hybrid seeds using *C. annuum* as the male plant and *C. baccatum* as the female parent.

The inventors used two molecular markers and morphological observations to confirm the interspecific nature of the HF1 hybrids obtained. In particular, the scar marker CD (Djian-Capolalino et al., 2007 (10)) was used for resistance to nematodes and an internal marker was used for resistance to *Phytophthora*.

Figure 1:
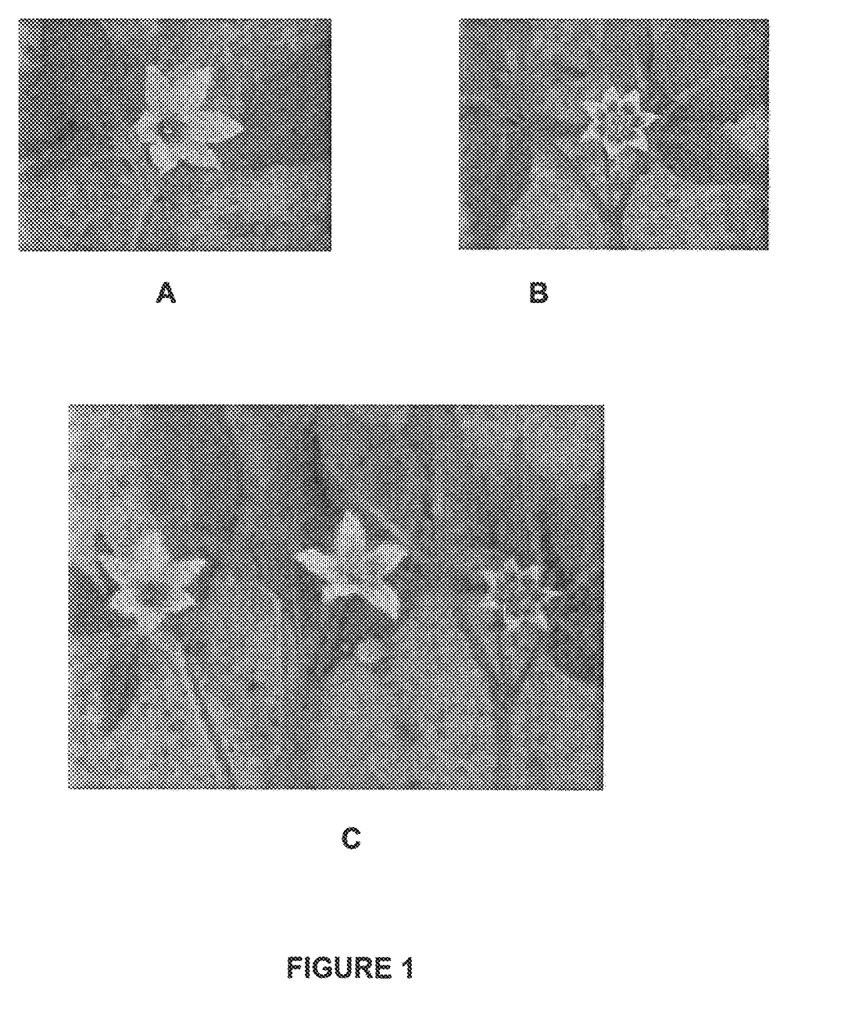
FIG. 1—*Capsicum* flowers

The *Capsicum annuum* plants used in these trials have a hairy stem and white flowers, while the *Capsicum baccatum* plants used have a glabrous stem and white flowers with yellow spots. The plants obtained after these crossings have a slightly hairy stem and flowers with light yellow spots (see FIG. 1), which confirms their hybrid character.

The inventors also determined that seven of the plants obtained from the crossings performed made it possible to obtain HF1 hybrids that combine the markers of resistance to nematodes with those to *Phytophthora* obtained from the accession CM334.

The results relating to three of the hybrids obtained are presented in table 4.

TABLE 4

HF1 hybrids obtained by crossing different *C. baccatum* plants (female parent) with *C. annuum* CM334 (male parent) and marking to determine their trait of resistance or susceptibility to nematodes and *Phytophthora*

| Crossing | Presence of fruit after hybridization | Presence of seeds in the hybrid fruit | Average number of HF1 seeds harvested per plant | Germintation of the HF1 seeds | Number of plants obtained from HF1 seeds | R nematodes (scar CD) | R *Phytophthora* | Interpretation |
|---|---|---|---|---|---|---|---|---|
| USDA PI 413669 01 SD*CM334 | X | X | 3.00 | X | 2.00 | R | heterozygote | hybrid |
| USDA PI 159252 01 SD*CM334 | X | X | 30.00 | X | 4.00 | R | heterozygote | hybrid |
| PEN79*CM334 | X | X | 80.00 | X | 2.00 | R | heterozygote | hybrid |

The inventors then crossed each of the seven hybrids obtained with either the recurrent *C. baccatum* parent (backcrossing) or the *C. baccatum* accession PBC1405 also identified as being valuable in particular in that it has excellent root vigour (level 5).

The seeds obtained from each crossing were harvested and "BC1" embryos were placed in culture. The embryo culture was performed according to the protocols of Dumas de Vaulx, 1992 (Dumas *Culture d'embryons et d'ovaires fécondés*. In: Jahier J. (ed) *Techniques de cytogénètique végétale*, INRA editions, page 141).

The number of seeds harvested by crossing and the number of plantlets obtained from these seeds were then determined. The inventors then produced a molecular marker screen for certain of the plants obtained for resistance to *Phytophthora* and nematodes. Four "BC1" plants having a double resistance to *Phytophthora* and nematodes were obtained.

The results relating to three of the hybrids are presented in tables 5 and 6.

TABLE 5

Characteristics of the Plants (BC1) obtained after crossing of the F1 Hybrids with either the *C. baccatum* plant used as the parent in the initial crossing or *C. baccatum* PBC1405

| Crossing | Number of seeds | Number of plantlets obtained | Number of plantlets tested | Number of R nematodes | Number of R *Phytophthora* | Number of double R |
|---|---|---|---|---|---|---|
| (USDA PI 413669 01 SD*CM334)*PI 413669 | 12 | 1 | 3 | 2 | 3 | 2 |

TABLE 5-continued

Characteristics of the Plants (BC1) obtained after crossing of the F1 Hybrids with either the
C. baccatum plant used as the parent in the initial crossing or C. baccatum PBC1405

| Crossing | Number of seeds | Number of plantlets obtained | Number of plantlets tested | Number of R nematodes | Number of R Phytophthora | Number of double R |
|---|---|---|---|---|---|---|
| (USDA PI 159252 01 SD*CM334)*PI 159252 | 4 | 2 | | | | |
| (USDA PI 159252 01 SD*CM334)*PBC 1405 | 29 | 18 | 11 | 7 | 3 | 2 |
| (PEN79*CM334)*PEN79 | 15 | 8 | 4 | 3 | 0 | 0 |

(R = resistance)

TABLE 6

Marking of plants resulting from the first backcrossing (BC1)

| No. | Variety | R. nematode (Me7) marking | R. phytophthora marking |
|---|---|---|---|
| 1 | (PEN79*CM334)*PEN79 | R | susceptible |
| 2 | (PEN79*CM334)*PEN79 | R | susceptible |
| 3 | (PEN79*CM334)*PEN79 | R | susceptible |
| 14 | (PEN79*CM334)*PEN79 | S | susceptible |
| 4 | (USDA PI 413669 01 SD*CM334)*USDA PI 413669 01 SD | S | Hetero. R |
| 5 | (USDA PI 413669 01 SD*CM334)*USDA PI 413669 01 SD | R | Hetero. R |
| 16 | (USDA PI 413669 01 SD*CM334)*USDA PI 413669 01 SD | R | Hetero. R |
| 7 | (USDA PI 159252 01 SD*CM334)*PBC1405 | S | susceptible |
| 8 | (USDA PI 159252 01 SD*CM334)*PBC1405 | S | susceptible |
| 9 | (USDA PI 159252 01 SD*CM334)*PBC1405 | R | susceptible |
| 10 | (USDA PI 159252 01 SD*CM334)*PBC1405 | R | susceptible |
| 11 | (USDA PI 159252 01 SD*CM334)*PBC1405 | ? | Hetero. R |
| 12 | (USDA PI 159252 01 SD*CM334)*PBC1405 | R | Hetero. R |
| 17 | (USDA PI 159252 01 SD*CM334)*PBC1405 | R | susceptible |
| 18 | (USDA PI 159252 01 SD*CM334)*PBC1405 | R | Hetero. R |
| 19 | (USDA PI 159252 01 SD*CM334)*PBC1405 | R | susceptible |
| 20 | (USDA PI 159252 01 SD*CM334)*PBC1405 | S | susceptible |
| 21 | (USDA PI 159252 01 SD*CM334)*PBC1405 | R | susceptible |

The inventors then performed a step of an additional crossing between "BC1" plants identified as being sensitive or resistant to *Phytophthora* and nematodes with *C. baccatum* ("BC2") plants followed by self-pollinations (BC1S1). The inventors produced a molecular marker screen for certain of the plants obtained for resistance to *Phytophthora* and nematodes. In addition to the marker already mentioned above, a second co-dominant scar marker, adapted to the marker described in Wang et al., 2009 (11) was also used for nematode resistance. The results obtained show that the two markers are related (3% of recombinations).

The segregations obtained are compatible with those expected on the basis of the level of resistance of the "BC1" plants of origin and the type of progeny ("BC2" or "BC1S1"). The results are shown in tables 7, 8 and 9.

TABLE 7

BC2 and BC1S1 data for the *Phytophthora* marking

| Code | State | Crossing | BC1 origin | prior results | number of plants R_R | R_S | S_S | % of plants % R:R | % R:S | % S:S |
|---|---|---|---|---|---|---|---|---|---|---|
| 10A6001-1DP1*10A5439 | BC2 | (PEN79*CM334)*PEN79*PEN79 | 1-D | susceptible | | | 1 | 0% | 0% | 100% |
| 10A6002-2DP1*10A5439 | BC2 | (PEN79*CM334)*PEN79*PEN79 | 2-D | susceptible | | | 1 | 0% | 0% | 100% |
| 10A6003-3DP1*10A5421 | BC2 | (PEN79*CM334)*PEN79*PBC1405 | 3-D | susceptible | | | 2 | 0% | 0% | 100% |
| 10A6006-9LP1*10A5421 | BC2 | (USDA PI 159252 01 SD*CM334)*PBC1405*PBC1405 | 9-L | susceptible | | | 42 | 0% | 0% | 100% |
| 10A6006-9LP1*10A5536 | BC2 | (USDA PI 159252 01 SD*CM334)*PBC1405*USDA PI 159252 01 SD | 9-L | susceptible | | | 52 | 0% | 0% | 100% |
| 10A6007-10MP1*10A5421 | BC2 | (USDA PI 159252 01 SD*CM334)*PBC1405*PBC1405 | 10-M | susceptible | | | 38 | 0% | 0% | 100% |
| 10A6007-10MP1*10A5536 | BC2 | (USDA PI 159252 01 SD*CM334)*PBC1405*USDA PI 159252 01 SD | 10-M | susceptible | | | 52 | 0% | 0% | 100% |

TABLE 7-continued

BC2 and BC1S1 data for the *Phytophthora* marking

| Code | State | Crossing | BC1 origin | prior results | number of plants R_R | R_S | S_S | % of plants % R:R | % R:S | % S:S |
|---|---|---|---|---|---|---|---|---|---|---|
| 10A6012-19YP1*10A5421 | BC2 | (USDA PI 159252 01 SD*CM334)*PBC1405*PBC1405 | 19-V | susceptible | | | 10 | 0% | 0% | 100% |
| 10A6013-21ABP1*10A5421 | BC2 | (USDA PI 159252 01 SD*CM334)*PBC1405*PBC1405 | 21-A | susceptible | | | 50 | 0% | 0% | 100% |
| Total | | | | | 0 | 0 | 248 | 0% | 0% | 100% |
| 10A6004-4HP1*10A5421 | BC2 | (USDA PI 413669 01 SD*CM334)*USDA PI 413669 01 SD*PBC1405 | 4-H | hetero | | | 11 | 0% | 0% | 100% |
| 10A6004-4HP1*10A5440 | BC2 | (USDA PI 413669 01 SD*CM334)*USDA PI 413669 01 SD*USDA PI 413669 01 SD | 4-H | hetero | | 1 | 2 | 0% | 33% | 67% |
| 10A6009-16VP1*10A5421 | BC2 | (USDA PI 413669 01 SD*CM334)*USDA PI 413669 01 SD*PBC1405 | 16-V | hetero | | 6 | 9 | 0% | 40% | 60% |
| 10A6009-16VP1*10A5440 | BC2 | (USDA PI 413669 01 SD*CM334)*USDA PI 413669 01 SD*USDA PI 413669 01 SD | 16-V | hetero | | 2 | 3 | 0% | 40% | 60% |
| Total | | | | | 0 | 9 | 25 | 0% | 26% | 74% |
| 10A6009-16VP1 | BC1S1 | F2[(USDA PI 413669 01 SD*CM334)*USDA PI 413669 01 SD] | 16-V | hetero | 2 | 6 | | 25% | 75% | 0% |
| 10A6011-18YP1 | BC1S1 | F2[(USDA PI 159252 01 SD*CM334)*PBC1405] | 18-V | hetero | 17 | 22 | 13 | 33% | 42% | 25% |
| Total | | | | | 19 | 28 | 13 | 32% | 47% | 22% |

TABLE 8

BC2 and BC1S1 data for the nematode marking (marker 1)

| Code | State | Crossing | BC1 origin | prior results | number of plants R | S | % of plants % R | % S |
|---|---|---|---|---|---|---|---|---|
| 10A6004-4HP1*10A5421 | BC2 | (USDA PI 413669 01 SD*CM334)*USDA PI 413669 01 SD*PBC1405 | 4-H | susceptible | | 14 | 0% | 100% |
| 10A6004-4HP1*10A5440 | BC2 | (USDA PI 413669 01 SD*CM334)*USDA PI 413669 01 SD*USDA PI 413669 01 SD | 4-H | susceptible | | 3 | 0% | 100% |
| Total | | | | | 0 | 17 | 0% | 100% |
| 10A6001-1DP1*10A5439 | BC2 | (PEN79*CM334)*PEN79*PEN79 | 1-D | resistant | | 1 | 0% | 100% |
| 10A6002-2DP1*10A5439 | BC2 | (PEN79*CM334)*PEN79*PEN79 | 2-D | resistant | | 1 | 0% | 100% |
| 10A6003-3DP1*10A5421 | BC2 | (PEN79*CM334)*PEN79*PBC1405 | 3-D | resistant | 1 | 1 | 50% | 50% |
| 10A6006-9LP1*10A5421 | BC2 | (DSDA PI 159252 01 SD*CM334)*PBC1405*PBC1405 | 9-L | resistant | 26 | 19 | 58% | 42% |
| 10A6006-9LP1*10A5536 | BC2 | (USDA PI 159252 01 SD*CM334)*PBC1405*USDA PI 159252 01 SD | 9-L | resistant | 20 | 32 | 38% | 62% |
| 10A6007-10MP1*10A5421 | BC2 | (USDA PI 159252 01 SD*CM334)*PBC1405*PBC1405 | 10-M | resistant | 15 | 25 | 38% | 63% |
| 10A6007-10MP1*10A5536 | BC2 | (USDA PI 159252 01 SD*CM334)*PBC1405*USDA PI 159252 01 SD | 10-M | resistant | 18 | 34 | 35% | 65% |
| 10A6009-16VP1*10A5421 | BC2 | (USDA PI 413669 01 SD*CM334)*USDA PI 413669 01 SD*PBC1405 | 16-V | resistant | 11 | 4 | 73% | 27% |
| 10A6009-16VP1*10A5440 | BC2 | (USDA PI 413669 01 SD*CM334)*DSDA PI 413669 01 SD*USDA PI 413669 01 SD | 16-V | resistant | 2 | 3 | 40% | 60% |
| 10A6012-19YP1*10A5421 | BC2 | (USDA PI 159252 01 SD*CM334)*PBC1405*PBC1405 | 19-V | resistant | 7 | 5 | 58% | 42% |

TABLE 8-continued

BC2 and BC1S1 data for the nematode marking (marker 1)

| Code | State | Crossing | BC1 origin | prior results | number of plants R | number of plants S | % of plants % R | % of plants % S |
|---|---|---|---|---|---|---|---|---|
| 10A6013-21ABP1*10A5421 | BC2 | (USDA PI 159252 01 SD*CM334)*PBC1405*PBC1405 | 21-A | resistant | 25 | 26 | 49% | 51% |
| Total | | | | | 125 | 151 | 45% | 55% |
| 10A6009-16VP1 | BC1S1 | F2[(USDA PI 413669 01 SD*CM334)*USDA PI 413669 01 SD] | 16-V | resistant | 4 | 4 | 50% | 50% |
| 10A6011-18YP1 | BC1S1 | F2[(USDA PI 159252 01 SD*CM334)*PBC1405] | 18-V | resistant | 35 | 15 | 70% | 30% |
| Total | | | | | 39 | 19 | 67% | 33% |

TABLE 9

BC2 and BC1S1 data for the nematode marking (marker 2)

| Code | State | Crossing | BC1 origin | prior results | R_R | R_S | S_S | % R:R | % R:S | % S:S |
|---|---|---|---|---|---|---|---|---|---|---|
| 10A6004-4HP1*10A5421 | BC2 | (USDA PI 413669 01 SD*CM334)*USDA PI 413669 01 SD*PBC1405 | 4-H | susceptible | | | 13 | 0% | 0% | 100% |
| 10A6004-4HP1*10A5440 | BC2 | (USDA PI 413669 01 SD*CM334)*USDA PI 413669 01 SD*USDA PI 413669 01 SD | 4-H | susceptible | | | 3 | 0% | 0% | 100% |
| Total | | | | | 0 | 0 | 16 | 0% | 0% | 100% |
| 10A6001-1DP1*10A5439 | BC2 | (PEN79*CM334)*PEN79*PEN79 | 1-D | resistant | | | | | | |
| 10A6002-2DP1*10A5439 | BC2 | (PEN79*CM334)*PEN79*PEN79 | 2-D | resistant | | | | | | |
| 10A6003-3DP1*10A5421 | BC2 | (PEN79*CM334)*PEN79*PBC1405 | 3-D | resistant | | 1 | 1 | 0% | 50% | 50% |
| 10A6006-9LP1*10A5421 | BC2 | (USDA PI 159252 01 SD*CM334)*PBC1405*PBC1405 | 9-L | resistant | | 26 | 18 | 0% | 59% | 41% |
| 10A6006-9LP1*10A5536 | BC2 | (USDA PI 159252 01 SD*CM334)*PBC1405*USDA PI 159252 01 SD | 9-L | resistant | | 20 | 31 | 0% | 39% | 61% |
| 10A6007-10MP1*10A5421 | BC2 | (USDA PI 159252 01 SD*CM334)*PBC1405*PBC1405 | 10-M | resistant | | 14 | 22 | 0% | 39% | 61% |
| 10A6007-10MP1*10A5536 | BC2 | (USDA PI 159252 01 SD*CM334)*PBC1405*USDA PI 159252 01 SD | 10-M | resistant | | 19 | 27 | 0% | 41% | 59% |
| 10A6009-16VP1*10A5421 | BC2 | (USDA PI 413669 01 SD*CM334)*USDA PI 413669 01 SD*PBC1405 | 16-V | resistant | | 9 | 4 | 0% | 69% | 31% |
| 10A6009-16VP1*10A5440 | BC2 | (USDA PI 413669 01 SD*CM334)*USDA PI 413669 01 SD*USDA PI 413669 01 SD | 16-V | resistant | | 2 | 1 | 0% | 67% | 33% |
| 10A6012-19YP1*10A5421 | BC2 | (USDA PI 159252 01 SD*CM334)*PBC1405*PBC1405 | 19-V | resistant | | 4 | 4 | 0% | 50% | 50% |
| 10A6013-21ABP1*10A5421 | BC2 | (USDA PI 159252 01 SD*CM334)*PBC1405*PBC1405 | 21-A | resistant | 4 | 15 | 13 | 13% | 47% | 41% |
| Total | | | | | 4 | 110 | 121 | 2% | 47% | 51% |
| 10A6009-16VP1 | BC1S1 | F2[(USDA PI 413669 01 SD*CM334)*USDA PI 413669 01 SD] | 16-V | resistant | 1 | 3 | 4 | 13% | 38% | 50% |
| 10A6011-18YP1 | BC1S1 | F2[(USDA PI 159252 01 SD*CM334)*PBC1405] | 18-V | resistant | 12 | 22 | 12 | 26% | 48% | 26% |
| Total | | | | | 13 | 25 | 16 | 24% | 46% | 30% |

REFERENCES

1. Erard P. & Odet J., 2009, *Le poivron—Intérêt et limite du greffage*, Infos-Ctifl 238:31-35
2. Palada M. C. & Wu D. L., 2008, *Evaluation of Chili Rootstocks for Grafted Sweet Pepper Production during the Hot-wet and Hot-dry Seasons in Taiwan*, Proc. XXVII IHC-S11 Sustain. Through Integr. And Org. Hort., pp. 151-157
3. Ribeiro et al., 2003, *Evaluation of Capsicum spp. Genotypes for resistance to Phytophthora capsici in Brazil*, Capsicum and Eggplant Newsletter 22:125-126

4. Yoon J. B. et al., 2009, *Inheritance of Anthracnose (Colletotrichum acutatum) Resistance in Capsicum using Interspecific Hybridization*, Kor. J. Hort. Sci. Technol. 27(1):140-144
5. Egawa Y. & Tanaka M., 1986, *Cytogenetical Study of the Interspecific Hybrid between Capsicum annuum and C. baccatum*, Japan. J. Breed., 36:16-21
6. Jones M. M. & Black L. L., 1992, *Sources of Resistance among Capsicum spp. to Fusarium Wilt of Pepper*, Capsicum Newsletter 11:33-34
7. Ortega G., et al., 1990, *Search for Verticillium dahliae resistance in Capsicum sp.*, Capsicum Newsletter 8-9:60-61
8. Muhyi R. & Bosland P., 1995, *Evaluation of Capsicum Germplasm for Sources or Resistance to Rhizoctonia solani*, HortScience, 30(2):341-342
9. Dumas de Vaulx, 1992, *Culture d'embryons et d'ovaires fécondés*. In: Jahier J. (ed) Techniques de cytogénétique végétale, INRA éditions, pp. 141
10. Djian-Caporalino C. et al., 2007, *Root-knot nematode (Meloidogyne spp.) Me resistance genes in pepper (Capsicum annuum L.) are clustered on the P9 chromosome*, Theor. Appl. Genet. 114:473-486
11. Wang L. H. et al., 2009, *A SCAR marker linked to the N gene for resistance to root knot nematodes (Meloidogyne spp.) in pepper (Capsicum annuum L.)*, Scientia. Horticulturae 122:318-322.

The invention claimed is:

1. A *Capsicum baccatum* plant suitable for use as a rootstock, obtained from the initial crossing of a *Capsicum annuum* plant, used as the male parent, with a *Capsicum baccatum* plant used as the female parent, wherein the initial crossing is followed by at least one additional crossing with a *Capsicum baccatum* plant, and wherein said *Capsicum baccatum* plant suitable for use as a rootstock has at a given crop stage, a root volume, a root mass or a hypocotyl height that is 10% greater than those of the TECNICO variety at the same stage, cultivated under identical conditions.

2. A *Capsicum baccatum* plant suitable for use as a rootstock, obtained from the initial crossing of a *Capsicum annuum* plant, with a first *Capsicum baccatum* plant, wherein the initial crossing is followed by at least one additional crossing with a *Capsicum baccatum* plant, and wherein said *Capsicum baccatum* plant suitable for use as a rootstock has at a given crop stage, a root volume, a root mass or a hypocotyl height that is 10% greater than those of the TECNICO variety at the same stage, cultivated under identical conditions.

3. A plant according to claim 1, wherein the *Capsicum baccatum* plant used in said at least one additional crossing is identical to the *Capsicum baccatum* plant used in the initial crossing.

4. A plant according to claim 1, wherein the *Capsicum baccatum* plant used in said at least one additional crossing is different from the *Capsicum baccatum* plant used in the initial crossing.

5. A plant according to claim 1, wherein said *Capsicum annuum* plant comprises at least one trait of agronomic interest, and wherein said at least one crossing is followed by a step of selecting plants comprising said trait of agronomic interest.

6. A plant according to claim 5, wherein said trait of agronomic interest is resistance to a pathogen.

7. A plant according to claim 6, wherein said pathogen is *Ralstonia solanacearum, Rhizoctonia solani, Pythium* spp., *Fusarium oxysporum, Phytophthora capsici, Sclerotium rolfsii, Verticillium albo-atrum, Verticillium dahliae, Meloidogyne incognita, Meloidogyne arenaria, Meloidogyne javanica, Meloidogyne hapla* or *Meloidogyne enterolobii*; or a PMMV, TMV, TSWV or PVY virus.

8. A plant according to claim 1, wherein said *Capsicum baccatum* plant used in said crossing(s) comprises at least one trait of agronomic interest, and wherein said at least one crossing is followed by a step of selecting plants comprising said trait of agronomic interest.

9. A plant according to claim 5, wherein the selection of plants comprising said trait of agronomic interest is performed by means of a phenotypic selection or by the use of molecular markers.

10. A *Capsicum baccatum* plant according to claim 1, further comprising intermediate resistance to *Phytophthora capsici* and intermediate resistance to *Meloidogynes* wherein said resistances are traits derived from *Capsicum annuum*.

11. A seed of a plant according to claim 1.

12. A cell of a plant according to claim 1.

13. A part of a plant according to claim 1.

14. A method of obtaining a grafted plant comprising using a *Capsicum baccatum* plant according to claim 1 as a rootstock and obtaining the grafted plant from said *Capsicum* plant.

15. The method of claim 14, further comprising grafting a graft on to the *Capsicum baccatum* plant according to claim 1.

16. The method of claim 15, wherein said graft is a plant of the *Capsicum* genus.

17. A method for obtaining a *Capsicum baccatum* plant suitable for use as a rootstock according to claim 1, or a part, cell or seed thereof, said method comprising the initial crossing of a *Capsicum annuum* plant used as the male parent, with a *Capsicum baccatum* plant used as the female parent, wherein the initial crossing is followed by at least one additional crossing with a *Capsicum baccatum* plant, and recovering said plant or part, cell or seed thereof, wherein said *Capsicum baccatum* plant suitable for use as a rootstock has at a given crop stage, a root volume, a root mass or a hypocotyl height that is 10% greater than those of the TECNICO variety at the same stage, cultivated under identical conditions.

* * * * *